United States Patent [19]

Jacobson et al.

[11] Patent Number: 5,098,996

[45] Date of Patent: Mar. 24, 1992

[54] PROCESS FOR INTRODUCING FLUORINE INTO BIOLOGICALLY ACTIVE MATERIALS

[75] Inventors: Kenneth A. Jacobson, Silver Spring; Kenneth L. Kirk; David C. Furlano, both of Bethesda; Yechiel Shai, Silver Spring, all of Md.

[73] Assignee: The United States of America as represented by the Department of Health and Human Services, Washington, D.C.

[21] Appl. No.: 168,494

[22] Filed: Mar. 15, 1988

Related U.S. Application Data

[63] Continuation-in-part of Ser. No. 874,143, Jun. 13, 1986, abandoned, which is a continuation-in-part of Ser. No. 664,953, Oct. 26, 1984, abandoned, and a continuation-in-part of Ser. No. 833,035, Feb. 26, 1986, abandoned, which is a continuation-in-part of Ser. No. 717,624, Mar. 24, 1983, abandoned.

[51] Int. Cl.$^5$ .......................... C07K 1/02; C07K 7/40; C07D 473/06; C07H 19/168
[52] U.S. Cl. ..................................... 530/303; 530/345; 424/1.1; 536/26; 544/271; 544/276; 560/41; 562/438; 564/184; 564/185
[58] Field of Search .................. 530/303, 345; 536/26; 548/503; 562/438; 564/184, 185; 560/41; 544/271, 276; 424/1.1; 930/22; 544/276

[56] References Cited

U.S. PATENT DOCUMENTS

| | | | |
|---|---|---|---|
| 3,825,553 | 7/1974 | Diamond et al. | 560/41 |
| 4,279,887 | 7/1981 | Baldwin et al. | 564/184 |
| 4,617,386 | 10/1986 | Elmaleh et al. | 536/18.4 |
| 4,647,446 | 3/1987 | Sargent, III et al. | 424/1.1 |
| 4,647,447 | 3/1987 | Gries et al. | 424/9 |

OTHER PUBLICATIONS

Morrison and Boyd, Organic Chemistry, 3rd edition, (Boston, Allen and Bacon, 1979), pp. 1148 to 1149.
Fieser and Fieser, Reagents for Organic Synthesis [New York, John Wiley and Sons, 1967], pp. 485 to 487.

Primary Examiner—Mukund J. Shah
Assistant Examiner—E. C. Ward
Attorney, Agent, or Firm—Birch, Stewart, Kolasch & Birch

[57] ABSTRACT

Radioactive fluorine can be easily introduced into biologically active molecules containing amino groups. A p-bromomethyl benzoyl group is coupled to the amino group of the biologically active molecule, and bromine is displaced by fluorine. Alternatively, the bromine on the bromomethylbenzoyl group is first displaced by fluorine, and the fluoromethyl benzoyl group is then coupled to the amino group of the biologically active molecule. The compounds so produced are useful in diagnostic nuclear medicine.

26 Claims, 1 Drawing Sheet

PROCESS FOR INTRODUCING FLUORINE INTO BIOLOGICALLY ACTIVE MATERIALS

BACKGROUND OF THE INVENTION

This application is a continuation-in-part of our copending application Ser. No. 874,143, filed June 13, 1986, which is a continuation-in-part of Ser. No. 664,953, filed Oct. 26, 1984; and Ser. No. 833,035, filed Feb. 26, 1986, which is a continuation-in-part of Ser. No. 717,624, filed Mar. 24, 1983 all now abandoned.

FIELD OF THE INVENTION

The present invention related to diagnostic medicine, and more particularly to a chemical method for introducing radioisotopic fluorine into biologically active molecules for use in diagnostic nuclear medicine.

In the four copending applications above, there are disclosed functionalized congeners of N6-phenyladenosine and 1,3-dialkyl-8-phenyl xanthine and in which a spacer chain terminating in a chemical functional group is inserted at the para position of the phenyl for the purpose of enhancing the binding properties of the functionalized congener to the A-1- adenosine receptor site or the A-2 adenosine receptor, depending upon the properties of the drug portion or primary pharmacophore of the molecule. In the case of adenosine the pharmacophore is an agonist. In the case of xanthine the pharmacophore is an antagonist. Both adenosine and xanthine derivatives bind competitively to A-1 and A-2 adenosine receptors.

The use of radioisotopes to label organic compounds for use in diagnostic nuclear medicine is well documented in the literature. Radioiodinated human serum albumin, fatty acids and triglycerides, as well as orthoiodohippuric acid, are among the compounds that have been used for such diagnostic purposes. It has been found that certain radiolabelled compounds will localize in the brain, heart, or in other target organs or tissues to a sufficient level to allow for imaging thereof. There has been increasing interest in finding compounds which will more effectively cross the blood-brain barrier, thus facilitating more efficacious imaging of the brain. $^{18}$Fluorine is a positron-emitting isotope which has a half-life of 110 minutes, and has been used extensively as a non-invasive in vivo tracer.

$^{18}$F positron emission tomography has been particularly effective in the study of brain metabolism and in scanning receptors and sites of drug uptake. The reactions through which $^{18}$F is introduced into a molecule include nucleophilic displacement of alkyl triflates, aromatic nucleophilic attack, and halogenation of phenols, olefins, and metallo-organics.

SUMMARY OF THE INVENTION

It is an object of the present invention to overcome deficiencies in the prior art, such as indicated above.

Other objects of the invention are to provide improvements in diagnostic nuclear medicine, and to provide improved brain imaging.

It is a further object of the present invention to provide compounds and a general methodology for rapid introduction of radioactive fluorine into peptides and functionalized drugs.

It is yet another object of the present invention to provide compounds which are useful in radiotracing, including positron emission tomography scanning.

According to the present invention, a p- bromomethyl benzoyl (BMB) group is coupled to an amino group, including a peptide amino group, via its N- hydroxysuccinimide ester. In a subsequent step, bromide is displaced by fluoride to produce the p- fluoromethylbenzoyl (FMB) group, under conditions compatible for use with 18F radiotracers.

Alternatively, a functionalized bromomethyl benzoyl group is initially fluorinated, and then is coupled to a functionalized drug, or to a biopolymer, or to any other compound in which a fluoride is to be incorporated.

Benzylic electrophilic centers are subject to attack by active nucleophiles, including "naked" fluoride ion in non-aqueous media.

Benzyl bromide substituted in the para position by an electron-withdrawing substituent is subject to rapid displacement by fluoride ion, and the resulting benzyl fluoride is relatively stable in aqueous medium. Due to the electron withdrawing effects of the carbonyl group substitution by fluoride through an SN2 mechanism is favored. Moreover, benzyl halides are not subject to elimination, which has been noted as a side reaction with other methods of introducing $^{18}$F.

Although the benzyl bromide derivatives are sufficiently reactive towards $^{18}$F anion in minute concentrations in most circumstances, the reactivity may be increased further by substituting more active leaving groups for bromide. For example, O-sulfonate esters of p-hydroxymethyl benzoyl derivatives (eg. mesyl, brosyl, etc.) may be used.

Fluorine is introduced according to the present invention using the following Scheme 1:

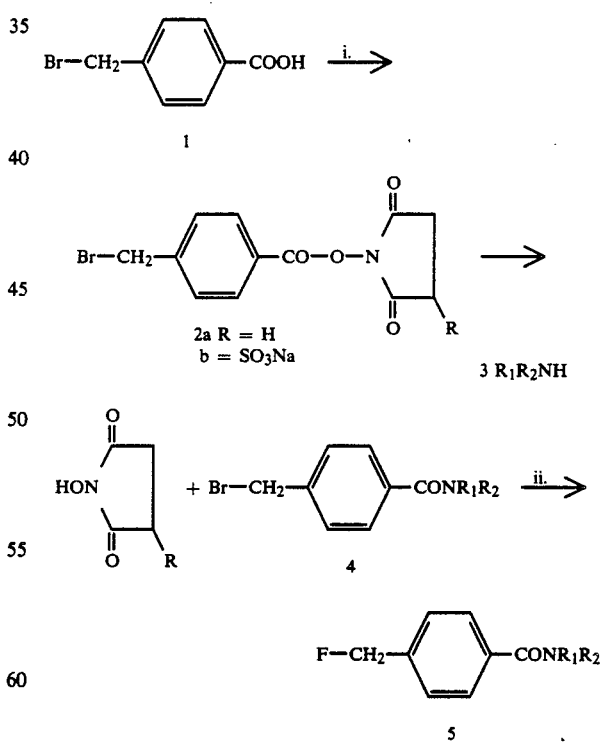

DETAILED DESCRIPTION OF THE INVENTION

Figure 1:
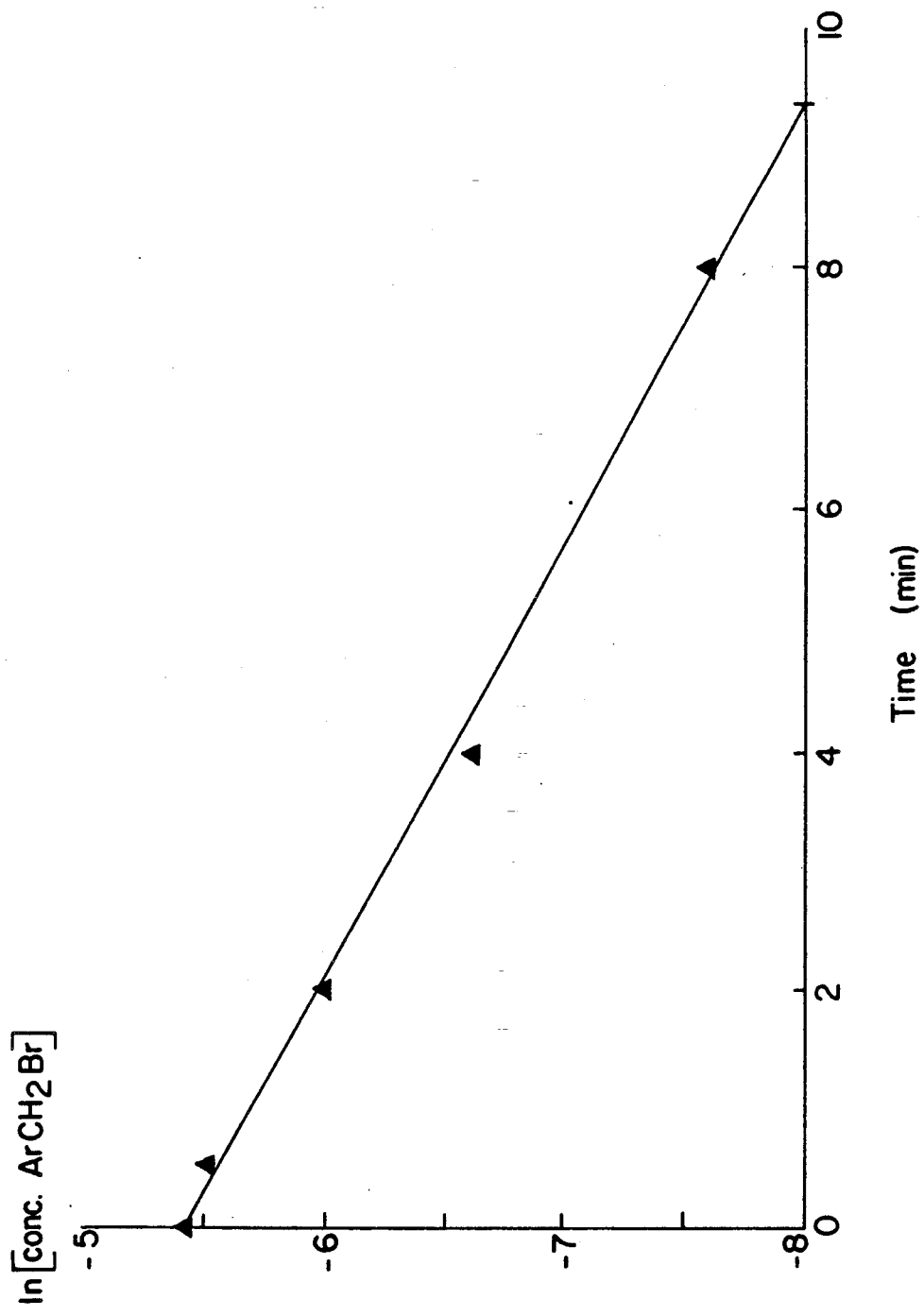
FIG. 1 shows the kinetics of displacement by fluoride (Bu$_4$N+F—$^3$) of p-bromomethy benzoyl methylamide, in acetonitrile at 23° C.

According to the present invention, the p-boromoethyl benzoyl (BMB) group is coupled to amino groups, including peptide amino groups, via its N-hydroxysuccinimide ester or other standard method of condensation.

Subsequently, the bromide is displaced by fluoride, which, in the preparation of radiotracers, is $^{18}$fluoride. The product is the corresponding p-fluoromethylbenzoyl (FMB) derivative.

Alternatively, a functionalized bromomethyl benzoyl group is initially fluorinated, and is then coupled to a compound in which a fluorine is to be incorporated, such as a functionalized drug or a biopolymer.

Referring to scheme 1, p-bromomethylbenzoic acid, compound 1, was preactivated as an active ester prior to coupling to amines. N-Succinimidyl-p- (bromomethyl)-benzoate, compound 2a, was prepared by condensing N-hydroxysuccinimide and α-bromo-p-toluic acid in 1:1 dimethylformamide/ethyl acetate using one equivalent of dicyclohexylcarbodiimide. After the insoluble urea which formed was removed by filtration, petroleum ether was added to precipitate the product, which had a melting point of 150°-153° C., in 70% yield. Analysis ($C_{12}H_{10}NO_4Br$): calculated 46.18% C, 3.23% H, 4.49% N; found, 46.24% C, 3.25% H, 4.49% N.

In stoichiometric equivalent amounts, this active ester efficiently and selectively acylated aliphatic and aromatic amino groups, with little competing N-alkylation.

The more water-soluble sulfosuccinimidyl ester, compound 2b, melting point >300° C., was also prepared, in 89% yield.

Alternative methods for coupling bromomethylbenzoic acid include use of carbodiimides, acid halides, mixed anhydrides, and symmetric anhydrides. For example, the symmetric anhydride of bromomethylbenzoic acid (mp 178°-179° C.) reacts readily with amines.

Following coupling to amines as above, the bromide of the resulting amide compound 4 was displaced in dilute solution (less than 1 mM) in refluxing acetonitrile in the presence of excess tetraalkylammonium fluoride or KF (in the presence of a potassium chelator, such as Kryptofix or a crown ether). Timed studies using the N-methylamide compound 4a and a five-fold excess of fluoride showed the $t_{\frac{1}{2}}$ of conversion to the benzyl fluoride to be less than one minute. The reaction was carried out using $^{18}F^-$, prepared from a target of $^{17}O$ water, and dried azeotropically by evaporation of acetonitrile. $^{18}F$ was the limiting reagent. Yields of radioactive FMB derivatives were generally between 10% and 70%.

The resulting p-fluoromethylbenzoylamino (FMB) derivatives, 5, were not active alkylating agents, as evidenced by non-reactivity towards aryl thiolates. Thus FMB derivatives tend to be stable in biological systems.

Table 1 shows representative model amino acid and peptide derivatives that have been subjected to the reaction of the present invention.

TABLE 1

Yields for acylation of amines by 2 and for fluoride displacement at 50° C. as determined using gas or high pressure liquid chromatography.

| 3 = | 4: % yield | mp °C. | 5: % yield | mol. ion[A] |
|---|---|---|---|---|
| a  $H_2NCH_3$ | 81 | 136–140 | 95[C] | 168 |
| b  $H_2N(CH_2)_3CH_3$ | 89 | 110 | 79[C] | 210 |
| c  $H_2N(CH_2)_2$—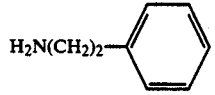 | 91 | 125–129 | >80 | 258 |
| d  $H_2N(CH_2)_2$—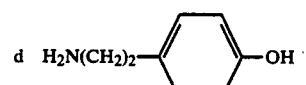—OH | 66 | 144–147 | 65 | 274 |
| e  $H_2N(CH_2)_2$—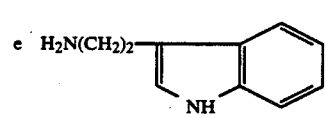 | 45[B] | oil | 75 | 297 |
| f  $H_2N$—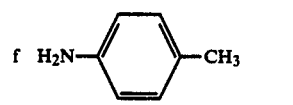—$CH_3$ | 94 | 184–186 | 63 | 232 |
| g  $H_2NCH_2CHOHCH_3$ (R) | 69[B] | 88–90 | 34 | 212 |
| h  $H_2NCHCH_3CH_2OH$ (S) | 76[B] | 130–1 | 89 | 212 |
| i  $H_2NCH(C_6H_5)CH_2OH$ (R) | 84[B] | 171–3 | 51 | 274 |
| j  $H_2NCH(C_6H_5)CH_3$ (R) | 63[B] | 137–8 | >90 | 258 |
| k  H—Gly—$NH_2$ | 60[B] | oil | >90 | 211 |
| l  H—Leu—$NH_2$ | 50[B] | oil | 54 | 267 |
| m  H—Ala—Gly—OH | 63[B] | 290d | 50 | 343 |

TABLE 1-continued

Yields for acylation of amines by 2 and for fluoride displacement at 50° C. as determined using gas or high pressure liquid chromatography.

| 3 = | 4: % yield | mp °C. | 5: % yield | mol. ion[A] |
|---|---|---|---|---|
| n  H—Phe—Phe—Gly—Leu—Met—NH$_2$ | 79[B] | — | 60 | — |

[A] By CI mass spectrometry (NH$_3$), value equals m + 1 unless noted.
[B] From (2b), aqueous reaction medium.
[C] Yield determined by GC.

An alternative route to the precursor p-bromomethylbenzoyl derivatives of peptides involves initial coupling of 4-hydroxymethylbenzoic acid (Chemical Dynamics Corp., South Plainfield, N.J.) to the peptide followed by conversion of the hydroxymethyl group to methyl bromomethyl upon a short exposure to 30% HBr in acetic acid at room temperature.

However, certain peptide functional groups present complications in this scheme. For example, the presence of a cysteinyl residue would not permit isolation of a reactive bromomethylbenzoyl derivative. Other groups present in some peptides, such as disulfides, may not tolerate nucleophilic F−. In such cases, an alternative procedure requires initial fluorination of a functionalized BMB derivative, later to be coupled to a functionalized drug or to a biopolymer. α-Bromo-p-toluic acid in chloroform, was fluorinated and subsequently followed by coupled to an amine. However, the overall yields were low (typically less than 10%). In acetonitrile, the desired fluorination product, α-fluoromethylbenzoic acid, was not obtained. Instead, an insoluble polymer, poly(oxycarbonyl-1,4-phenylenemethylene) was obtained. Attempted fluorination of the active ester, 2a, resulted in decomposition.

An alternative procedure involves initial fluorination of 6, α-bromo-p-toluic acid t-butyl ester (using tetrabutylammonium fluoride in acetonitrile, 90% yield) followed by quantitative cleavage of the t-butyl ester by brief exposure (approx. 10 minutes) to trifluoroacetic acid to give α-fluoro-p-toluic acid, 8. This acid, already containing a fluorine is then coupled to an amine.

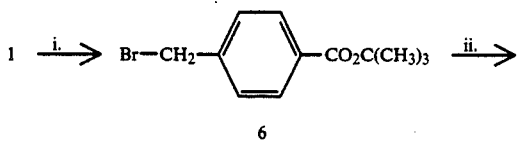

6

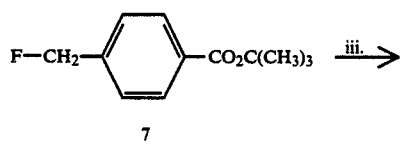

7

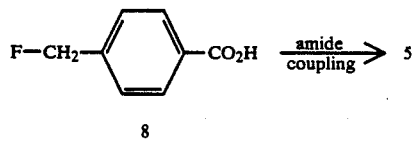

8

Scheme 2. reagents: i. isobutylene; ii. F−N+(Bu)$_4$/CH$_3$CH; iii. CF$_3$COOH.

Since the coupling of compound 8 to amines occurs with side reactions, alternative routes utilizing spacer chains were devised. Fluorination substrates containing spacer chains, such as alkyldiamines (Scheme 3) situated between the BMB moiety and the site of reaction with a functionalized drug were synthesized. The terminal reactive group for coupling to the drug may be of the electrophilic type (activated carboxylate, sulfonyl chloride, isothiocyanate, etc.) or of the nucleophilic type (principally an amine). An amino group may be blocked with a transient protecting group, eg. t- butyloxycarbonyl, to be removed following fluorination and prior to coupling to the functionalized drug. Prior to coupling this amino group it is often desirable to pre-activate the peptide or drug, eg. as an N-hydroxysuccinimide ester.

Two illustrations of how the spacer methodology has been utilized are given in Scheme 4. The first example (Compounds 9-14) includes an alkyl diamine as spacer. The second example used a spacer consisting of diethylenetriamine. A series of asymmetric urethane protected intermediates (Compounds 16-18) are synthesized to assure that the BMB group is attached at an unambiguous site. In the final coupling to a functionalized drug (present in excess), the primary amine reacts preferentially. Prosthetic group 21 has enhanced nucleophilicity and the product contains an additional amino group (sometimes desirable for solubility or affinity at the receptor).

Scheme 3. Use of prosthetic groups for radiofluorination. Functionalized receptor ligands, to which is coupled the prothetic group IV:

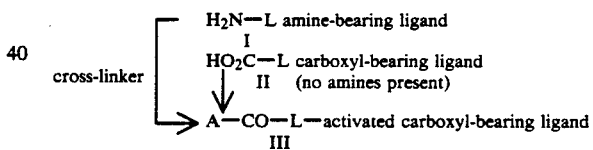

examples of homobifunctional cross-linker to convert I to III: disuccinimidyl suberate, disuccinimidyl adipate, disuccinimidyl tartrate, ethylene glycol-bis-(succinimidylsuccinate).

Prosthetic group for radiofluorination:

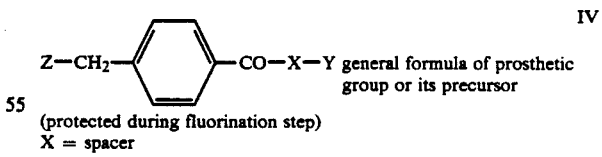

(protected during fluorination step)
X = spacer

X=spacer examples of spacers:  —NH—(CH$_2$)$_n$—    m,n = 0–6
—NH—(CH$_2$)$_m$—N(Boc)—(CH$_2$)$_n$—
—NH—(CH$_2$)$_m$—O—(CH$_2$)$_n$—

Y=reactive functional group (eg. —COOH or —NH$_2$), may be in a reversibly-protected form, such as t-butyloxycarbonyl-amino, or in an activated form, such as N-hydroxysuccinimide ester of a carboxylic acid.

Z = leaving group, such as bromo, iodo, mesylate, tosylate, brosylate, triflate, etc.

Scheme 4a

BmB = p-bromomethylbenzoyl, FMB = p-fluoromethylbenzoyl
n = 0-6

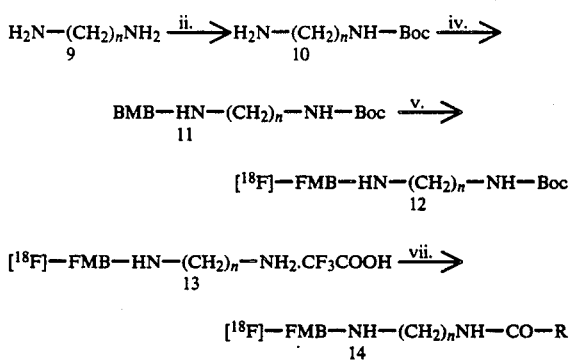

Scheme 4b

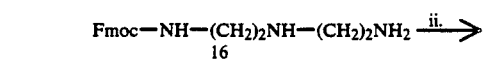

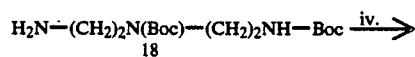

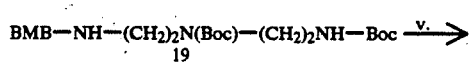

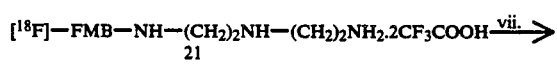

-continued
Scheme 4b

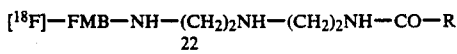

Reagents: i. 9-fluorenemethyloxychloroformate, ii. di-t-butyl-dicarbonate, iii. diethylamine, iv. α-bromotoluic acid/carbodiimide, v. 18-F-/K+/kryptofix, vi. trifluoracetic acid, vii. functionalized drug, derivatized as an activated carboxylic acid/tertiary amine.

For peptides and other substrates having limited solubility in acetonitrile, the fluorination reaction may be carried out in other non-reactive polar aprotic solvents such as tetrahydrofuran and dimethylformamide. DMSO was not a suitable solvent for the fluorination reaction, since the benzyl bromide group was reactive with this solvent.

High affinity ligands for adenosine receptors incorporating the bromomethylbenzoyl group have also been synthesized.

The bromomethylbenzoyl group may also be incorporated into certain 1,3-dialkylxanthine derivatives to give adenosine receptor antagonists. The following derivatives have been prepared and shown to bind to A1- adenosine receptors in rat brain membranes in competitive binding experiments using [3H]-N6-phenylisopropyladenosine as a radiotracer. In both cases the Ki is between $10^{-9}$ and $10^{-8}$ molar.

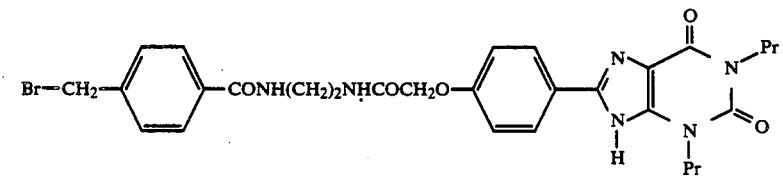

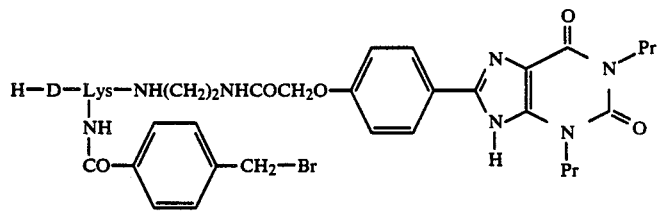

The feasability of attachment of the bromoethylbenzoyl prosthetic group in biological systems has been demonstrated. In addition to the many peptides which contain non-essential amino groups, some drug molecules may also be coupled to this prosthetic group without loss of receptor binding.

Other ligands labeled with $^{18}F$ through this methodology are listed in Table 2. Ligands for receptors for purines, catecholamines, and peptides are included. The synthetic route to 23 and 25 (adenosine derivatives) are given in Scheme 5. Scheme 6 outlines the route used to prepare $^{18}F$insulin.

A kinetic study of the rate of fluorine substitution, under pseudo-first order conditions, was carried out:

TABLE 2

Receptor ligands derivatized using prosthetic group for radiofluorination.

| Structure | Receptor | Ki-value in competitive binding assay |
|---|---|---|
| Purine derivatives: | | |

TABLE 2-continued

Receptor ligands derivatized using prosthetic group for radiofluorination.

| Structure | Receptor | Ki-value in competitive binding assay |
|---|---|---|
| 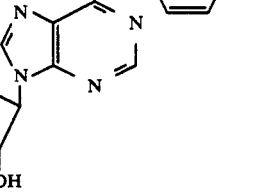 | | |
| 23. FMB—ADAC 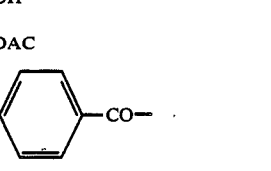 R = FCH$_2$—C$_6$H$_4$—CO— | A1 agonist | 10 nM (rat brain) |
| 24. FMB—Gly—ADAC 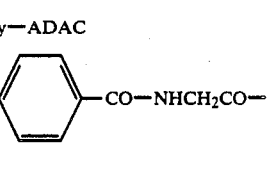 R = FCH$_2$—C$_6$H$_4$—CO—NHCH$_2$CO— | A1 agonist | 5 nM (mouse brain) |
| 25. FMB-aminoethyl-ADAC 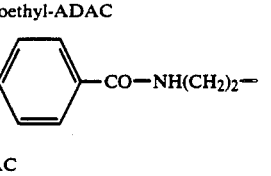 R = FCH$_2$—C$_6$H$_4$—CO—NH(CH$_2$)$_2$— | A1 agonist | 3 nM (rat) |
| 26. FMB—XAC 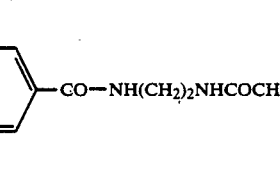 FCH$_2$—C$_6$H$_4$—CO—NH(CH$_2$)$_2$NHCOCH$_2$O—C$_6$H$_4$— | A1 antagonist | 12 nM (rat) |
| 27. FMB-aminoethyl-XAC 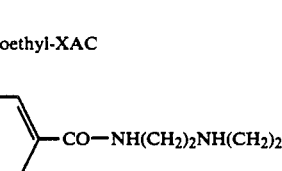 FCH$_2$—C$_6$H$_4$—CO—NH(CH$_2$)$_2$NH(CH$_2$)$_2$NHCOCH$_2$O—C$_6$H$_4$— | A-1,2 antagonist | 4 nM (rat) |
| Indole derivative: 28.  FCH$_2$—C$_6$H$_4$—CO—NHCH$_2$C(CH$_3$)$_2$NHCH$_2$CHOHCH$_2$O— | β-adrenergic antagonist | 10$^{-11}$ M |
| Peptide derivatives: | | |
| 29. N$^\alpha$—FMB—Arg—Pro—Lys—Pro—Gln—Gln—Phe—Phe—Gly—Leu—Met—NH$_2$ 1 nM (rat brain) | substance P | |
| N$^\alpha$—FMB—Asp—Tyr(SO$_3$)—Met—Gly—Trp—Met—Asp—Phe—NH$_2$ | cholecystokinin | 1n M |
| N—B1—FBM-suberoyl-insulin | inuline | 3 nM (lymphocytes) |

Scheme 5
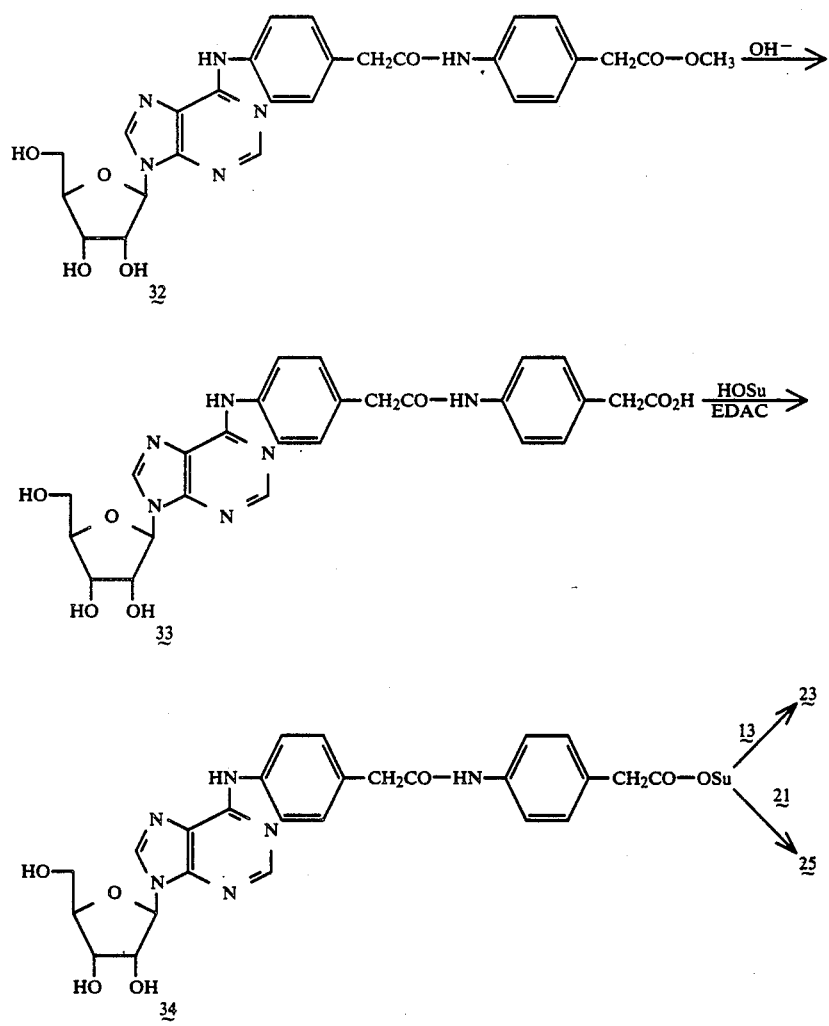
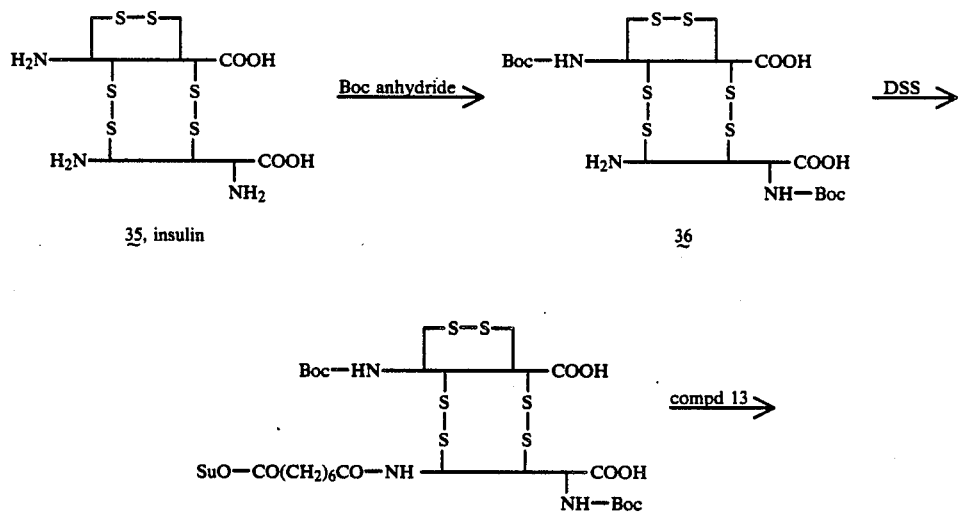

-continued

Scheme 6

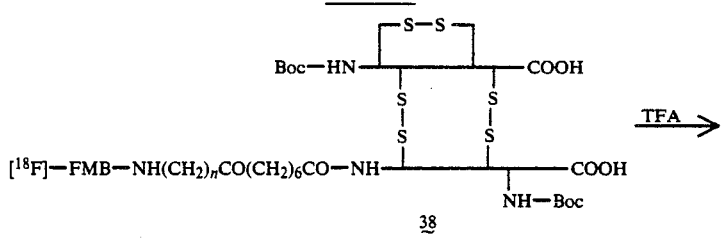

38

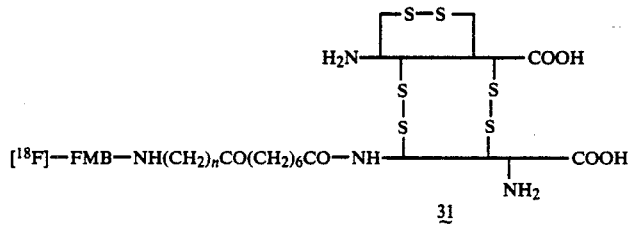

31

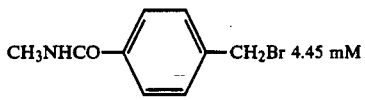

The temperature of the reaction was 23° C. in dry 1:1 acetonitrile/tetrahydrofuran. The t₁ of the reaction was 2.50 minutes. A rate constant (k2) of 0.554 M/min was obtained. This rate is sufficiently rapid for 18F substitution. In the reaction with radioactive fluoride, the bromo-derivative is the excess reagent. With the temperature elevated to 60° the reaction rate by roughly an order of magnitude. Thus, even lower concentrations than those used in this kinetic study suffice for the 18F time scale.

Mono-t-butyl oxy carbonyl-ethylene diamine, Compound 10 (n=2)

Two grams, 33.3 mmole, of ethylene diamine (Aldrich Chemical Co.) was dissolved in 10 ml of acetone. To this solution was added with stirring 726 mg, 3.33 mmole, of t-butyl oxycarbonyl anhydride (Pierce Co.). The reaction was carried out for five minutes. The excess of the ethylene diamine was removed by nitrogen, and the residue was chromatographed on silica gel using acetone as eluent. A band migrating at $R_f$0.25 was isolated as an oil and identified as the product by mass spectroscopy.

Mono-t-butyl oxycarbonyl diamino butane, Compound 10 (n=4) 25 Ten mmoles, 880 mg of 1,4-diamino butane (Fluka, A.G. Chem.) was dissolved in 2 ml acetone. Then 300 mg, 1.37 mmole, of di-t-butyloxycarbonyl anhydride was dissolved in 1 ml acetone, and was added by portions to the amine solution by stirring over a period of five minutes. One hundred ml of water was added, and an oil separated form the solution. The oil was redissolved in acetone and was chromatographed on a silica gel column, using acetone as eluent. A band migrating at $R_f$0.26 was isolated as an oil and identified as the product.

1-Bromomethylbenzoylamino-2-t-butyloxycarbonyl-(amino) ethane, Compound 11 (n=2)

Three hundred mg, 1.4 mmole, of bromomethylbenzoic acid (Aldrich) was dissolved in 5 ml acetonitrile, and 223 mg (1.4 mmole) of mono butyl ethylene diamine was added in portions with stirring A solution formed. Then, 1.6 ml of 1M DCC (in $CH_2Cl_2$) was added in portions, and the reaction proceeded for one hour. The precipitate was removed, and the acetonitrile was evaporated. A solid product was obtained, dissolved in acetone and chromatographed on silica gel using ethyl acetate:petroleum ether 3:2 as eluent. The yield was 200 mg, 38%. The mass spectrum ($CI-HH_3$) showed a molecular ion at 257 and 258 $^{M/2}$ corresponding to a fragment that lost the butyloxycarbonyl protecting group.

The product was identified by NMR. The purity was tested also by HPLC. Solvent A was 0.1% TEA in water; solvent B was 0.1% TFA in acetonitrile, using a gradient of 25% B to 80% B in 45 minutes. Rt=25.4 minutes, mp=147° C. o 1-Bromomethylbenzoylamino-2-t-butyloxycarbonylamino butane was prepared as above. The overall yield was 45%. The product, which had a melting point of 139° C., was identified by mass spectroscopy and NMR.

1-(Fluoromethylbenzoylamino)-2-(t-butyloxycarbonylamino) ethane, Compound 11 (n=2)

10 mg, 2.8 mmole, of bromomethylbenzoylamino was dissolved in 300 ml of dry acetonitrile. To the solution was added, with stirring, 28 ml (28 mmol) of tetramethylammonium fluoride solution in tetrahydrofuran. The reaction was heated to 50° C. for 10 minutes, and the product was separated on a thin layer silica plate. Rf=0.46, 3.2 ethyl acetate:petroleum ether. HPLC showed a clean product, $R_f$=20.6 minutes, using the gradient as for bromomethylbenzoyl.

FMB-Gly-Insulin $N^{\alpha,A1}$,$N^{\epsilon,B29}$ (BOC)₂ insulin, 537 mg, 89.5 mmole, was dissolved in 500 ml DMSO. FMB-Gly-OAS, 120 mg, 390 mmole in 20 ml DMSO, and 24.5 mg, 390 mmole in 2.5 ml DMSO , and 4-ethyl morpholine, 100 mg, 870 mmole in 10 ml DMSO, were added, and the reaction was allowed to remain at rom temperature for eighteen hours. The reaction was monitored by RP-HPLC until completion. One pure product was obtained, Rt=26 minutes . The eluting solvents were A, 0.1% TFA in water; B, 0.1% TFA in acetonitrile. Elution was made from 25% B to 80% in 45 minutes. The solution was lyophilized, and 50 ml neat TFA was added for five minutes, and then evaporated. The product reacted in an insulin-antibody binding assay.

$N^{\alpha,A1}$,$N^{\epsilon,B29}$ diboc,$N^{\alpha,B1}$N-hydroxy-succinimidyl-suberoyl) insulin, Compound 37

$N^{\alpha,A1},N^{\epsilon,B29}$ diBOCinsulin, 287 mg, 47.8 mmole in 60 ml DMSO was mixed with 88 mg, 239 mmole of disuccinimidylsuberate in 9 ml DMSO and 16.5 mg, 143 mmole 4-ethylmorpholine in 2 ml DMSO. The reaction was allowed to proceed for eighteen hours, and was monitored by R-P-HPLC. One pure product was obtained using solvent conditions as follows: Solvent A, 0.1% TFA in water; solvent B, 0.1% TFA in acetonitrile, gradient from 25% B to 80% B in 45 minutes.

The activity of the product was tested by reacting a sample with an excess of aminoethanol for five minutes. A pure new product was obtained with a shift in retention time from 24.5 to 22.5 minutes having the same area as the starting material, as judged by the HPLC profile.

$N^{\alpha B1}$(FMB-NHCH$_2$CH$_2$NH-suberoyl) insulin, compound 31

$N^{\alpha,A1},N^{\epsilon,B29}$ diboc, $N^{\alpha,B1}$N-hydroxy-succinimidoylsuberate), 100 mg, 16.6 mmole in 50 ml DMSO, was mixed with 16.2 mg, 80 mmole FMB-NHCH$_2$CH$_2$NH$_2$ in 5 ml DMSO and 50 mg, 434 mmole, N-ethyl morpholine. The reaction was heated to 50° C. for 20 minutes. Then, an excess of ethylene diamine was added, and the remaining active ester reacted with it to give a product which could be separated from the desired produced using HPLC, a shift of retention time from 22.8 to 20.1 minutes. The yield of the desired product was 60% as judged by peak areas. The product was lyophilized and treated for ten minutes in neat TFA. The TFA was then evaporated. The product was tested by antibody assay.

[$^{18}$F]-Fluoromethylbenzoylaminoethylamine, Compound 13, n=2

Three hundred mCi of $^{18}$F potassium fluoride, cyclotron produced, and Kryptofix 22 were dried azeotropically in CH$_3$CN. Two mg of BMB-NHCH$_2$CH$_2$NH-BOC (compound 11, n=2) was added to 0.5 ml of the acetonitrile solution, and the mixture was refluxed for one hour. Compound 12, n=2, [$^{18}$F]-FMB-NHCH$_2$CH$_2$NHBOC was separated chromatographically from the reaction in 66% radiochemical yield. A brief exposure of approximately five minutes to trifluoroacetic acid yielded [$^{18}$F]-FMB-NHCH$_2$CH$_2$NH$_2$.TFA, compound 13, n=2.

The [$^{18}$F]-amine derivative was coupled to various carboxyl-activated receptor ligands, and the products were separated by reversed phase HPLC, mobile phase 0.1% TFA in water/acetonitrile gradient. The coupling reactions to an adenosine-OSu ester, compound 34, and to insulin-suberoyl-OSu, compound 37, were carried out in DMSO in the presence of imidzaole. The $^{18}$F-derivatized insulin, compound 31, was obtained in 20–60% radiochemical yield in two steps, including a final TFA-deprotection. The HPLC retention time was identical to that of unlabelled compound 31.

Preparation of active esters of p-bromomethylbenzoic acid.

N-Succinimidyl p-(bromomethyl)benzoate, BMB-OSu (2a) was prepared by condensing N-hydroxysuccinimide and o-bromo-p-toluic acid (1, Aldrich Chemical Co., St. Louis MO) in DMF/ethyl acetate (1:1) using one equivalent of dicyclohexylcarbodiimide. After filtration of an insoluble urea, addition of petroleum ether caused precipitation of the product [10](2a), mp. 150°–153°, in 70% yield. Analysis (C$_{12}$H$_{10}$NO$_4$Br): calc. 46.18% C, 3.23% H, 4.49% N; found 46.24% C, 3.25% H, 4.49% N.

N-Sulfosuccinimidyl p-(bromomethyl)benzoate (2b), mp>300° C., was prepared in 89% yield by condensing N-hydroxysulfosuccinimide and $\alpha$-bromo-p-toluic acid (1, Aldrich Chemical Co., St. Louis, MO) in DMF by the method of Staros [11].

Coupling of active ester to amine.

In a typical coupling experiment, BMB-OSu, 2a (162 mg, 0.52 mmol) and 2-phenylethylamine (65 μL, 0.52 mmol) were combined in 3 ml DMF. After one hour the product (4c) was extracted into ethyl acetate, washed with acid/base, and recrystallized. A typical NMR spectrum in CD$_3$CN showed resonances at 7.74 and 7.49 (each d, 2H, J=8Hz, aryl) and 4.61 (s, 2H, benzylic) ppm.

Fluoride substitution reaction.

A BMB-amide (4) was dissolved in anhydrous acetonitrile (1 mg/ml) and treated with two equivalents of tetrabutylammonium fluoride (THF solution, Aldrich Chemical Co.). This acetonitrile solution was then dried by evaporation of the azeotrope. The anhydrous solution was heated for three minutes at 50° under a nitrogen atmosphere. The reaction could be followed by a thin layer chromatography (silica, ethyl acetate: petroleum ether, 1:1, R$_f$ values for BMB-methylamide, 4a, and FMB-methylamide, 5a, =0.48 and 0.43, respectively). Yields of FMB-amides (5) for the Table was determined by gas chromatography (OV-1 capillary column, J&W Scientific, Folson, CA) or by HPLC (Waters μ Porasil, 4.6×25 mm, using 20% ethylacetate/hexane or Beckman Ultrasphere ODS, medium, for 5k to 5m). Typical NMR spectrum (for 5a, CD$_3$CN) δ 7.78 and 7.43 (each d, 2H, J=8Hz), 5.40 (d, 2H, J=47Hz), 2.83 (d, 3H, J=4.5 Hz). Mp of 5a 113°–115°.

Preparation of $\alpha$-fluorotoluic acid.

4-Bromomethylbenzoic acid was converted to t-butyl 4-bromomethylbenzoate using isobutylene in sulfuric acid [16], in 50% yield. The product, an oil, had the following NMR spectrum in CDCl$_3$: δ 7.96 and 7.43 (each d, 2H, J=8Hz), 4.50 (s, 2H), 1.59 (s, 9H, t-Bu). The chemical ionization mass spectrum (NH$_3$) showed peaks at 211 (m+1), 228. The bromomethyl compound was fluorinated as above using tetrabutylammonium fluoride in acetonitrile, in 90% yield. NMR spectrum in CDCl$_3$: δ 8.01 and 7.41 (each d, 2H, J-8Hz), 5.44 (d, 2H, J=47Hz), 1.60 (s, 9H, t-Bu). The t-butyl ester was removed quantitatively upon 10 min exposure to neat trifluoroacetic acid. The product, $\alpha$-fluorotoluic acid, was obtained as a white solid, melting at 178°–181°. The chemical ionization mass spectrum (NH$_3$) showed a peak at 172=m+1+17). NMR spectrum in CDCl$_3$: δ 8.12 and 7.47 (each d, 2H, J=8Hz), 5.47 (d, 2H, J=47Hz).

Bromomethylbenzoyl-glycine t-butyl ester.

$\alpha$-Bromotoluic acid (5.93 g, 28 mmol) and glycine t-butyl ester hydrochloride (4.4 g, 26 mmol) and dicyclohexylcarbodiimide (6.23 g, 30 mmol) were added to 120 ml of DMF/ethyl acetate (1:1). Diisopropylethylamine (26 mmol) was added dropwise. The mixture was filtered, extracted with acid/base, and dried (Na$_2$SO$_4$). The organic solution was evaporated and triturated with petroleum ether with scratching to give white crystals (3.1 g, 36% yield). Mp 98°–102°.

Bromomethylbenzoyl-glycine. Bromomethylbenzoyl-glycine. t-butyl ester was treated with trifluoroacetic acid and the product, a solid melting at 162°–164°, was purified in 70% yield by preparative thin layer chromatography. NMR (CHCl$_3$) δ 8.86 (t, 1H, NH, J=5.8 Hz), 7.86 (d, 2H, Ar-2,6), 7.53 (d, 2H, Ar-3,5), 4.81 (s, 2H, CH$_2$Br), 3.91 (d, 2 H, J=5.9 Hz), 3.6 (br, 1H, COOH).

N-Succinimidyl bromomethylbenzoyl-glycine. Bromomethylbenzoyl-glycine was coupled to N-hydroxysuccinimide in DMF using EDAC. The product (60% yield) precipitated upon addition of water. Mp 174°–177°. NMR (CHCl$_3$) δ 7.81 (d, 2H, Ar-2,6, J=8.2Hz), 7.48 (d, 2H, Ar-3,5, J=8.2Hz), 6.60 (m, 1H, NH), 4.63 (d, 2H, CH2gly, J=5.5Hz), 4.61 (s, 2H, CH2Br), 2.87 (s, 4H).

Fluoromethylbenzoyl-glycine t-butyl ester. Bromomethylbenzoyl-glycine t-butyl ester was fluorinated in 90% yield using tetrabutylammonium fluoride in acetonitrile. NMR (CHCl$_3$) δ 7.84 (d, 2H, Ar-2,6, J=8.3Hz), 7.44 (d, 2H, Ar-3,5, J=7.9Hz), 6.66 (1H, NH), 5.44 (d, 2H, CH2F, J=47Hz), 4.15 (d, 2H, CH2gly, J=5.0Hz), 1.51 (9H, Bu).

Fluoromethylbenzoyl-glycine. Fluoromethylbenzoylglycine t-butyl ester was treated with trifluoroacetic acid for one hour, and the product was purified by thin layer chromatography. Mp 233°–235°.

N-Succinimidyl fluoromethylbenzoyl-glycine. Fluoromethylbenzoyl-glycine (17 mg, 81 μmol), N-hydroxysuccinimide (Pierce Chemical Co., Rockville, IL, 11 mg, 96 mol), and EDAC (30 mg, 0.15 mmol) were combined in 1 ml DMF. After one hour chloroform was added, and the solution was extracted with pH 7 phosphate buffer. The organic layer was dried (Na$_2$SO$_4$) and evaporated leaving the product as an oil (14.9 mg, 60% yield). NMR (CHCl$_3$) 6 7.85 (d, 2H, Ar-2,6, J=7.7Hz), 7.45 (d, 2H, Ar-3,5), 6.73 (m, 1H, NH), 5.49 (d, 2H, CH2F, J=47Hz), 4.63 (d, 2H, CH2gly, J=5.5Hz), 2.9 (4H).

9-Fluorenemethyloxycarbonyl-diethylenetriamine dihydrochloride., compound 16. Diethylenetriamine (Aldrich Chem. Co., 1.86 g, 18 mmol) in 20 ml ethanol was treated with 4 ml conc. HCl resulting in a precipitate. Water was added until a solution formed. A suspension of 9-fluorenemethylchloroformate in 20 ml ethanol was added in portions with stirring, alternating with addition of water to dissolve forming precipitate. After 1 hour, 1-propanol (75 ml) was added. The precipitate (diethylenetriamine trihydrochloride) was collected and discarded. The filtrate was evaporated to a small volume and the product, a white precipitate was collected. The product was recrystallized from methanol/ethyl acetate to give 1.58 g (67% yield). Mp. 180°–182° d.

Unsymmetrical Di-t-butyloxycarbonyl-(9-fluorenemethyloxycarbonyl)-diethylenetriamine., compound 17. 9-Fluorenemethyloxycarbonyl-diethylenetriamine dihydrochloride (0.13 g. 0.33 mmol), di-t-butyloxycarbonyl dicarbonate (0.21 g, 1 mmol), and N-methylmorpholine (0.1 ml, 0.91 mmol) were dissolved in 8 ml methanol. After one hour most of the solvent was evaporated and ether was added. After acid/base wash, the organic layer was dried (Na$_2$SO$_4$) and evaporated leaving a clear oil. Mass spectrum (CI-NH$_3$) shows a molecular ion at 526 and fragments corresponding to loss of urethane groups at 426, 326, 304, and 204 m/z.

Unsymmetrical Di-t-butyloxycarbonyl-diethylenetriamine., compound 18. Unsymmetrical Di-t-butyloxycarbonyl-(9-fluorenemethyloxycarbonyl)-diethylenetriamine was deprotected in a 20% solution of diethylamine in methanol. The product was isolated as an oil following evaporation, redissolving in methanol, and adding ether. R$_f$ (silica, chloroform:methanol:acetic acid, 85:10:5) 0.15.

Unsymmetrical N-(4-bromomethylbenzoyl)-di-t-butyloxycarbonyl-diethylenetriamine., compound 19. Unsymmetrical Di-t-butyloxycarbonyl-diethylenetriamine was treated with a molar excess of α-bromotoluic acid, and EDAC in dimethylformamide. After one hour, ether was added, and the organic layer was acid/base washed, dried (Na$_2$SO$_4$), and evaporated. The residue was chromatographed on silica gel (ethyl acetate:petroleum ether, 1:1). A band migrating at Rf 0.37 was isolated as an oil and identified as the product by CIMS (500, 456, 400, 358, 356, 302, 300 m/z) and by NMR.

N$^6$-(4-Carboxymethyl(phenyl(amino(4-carbonylmethylphenyl))))adenosine., compound 33. N$^6$-(4-Methyloxycarbonylmethyl(phenyl(amino(4-carbonylmethylphenyl))))adenosine (150 mg) was dissolved in 5 ml dimethylformamide and treated with 0.6 ml 1M Naoh. After 24 hours, the solution was acidified with citric acid and treated with saturated sodium chloride. The precipitate was collected by centrifugation and washed with water (3×), a small amount of cold methanol (2×), and ether. Yield 61 mg (42 Mp 182°–184°.

N-Succinimidyl-N$^6$-(4-Carboxymethyl(phenyl(amino(4-carbonylmethylphenyl)))adenosine., compound 34. N$^6$-(4-Carboxymethyl (phenyl(amino(4-carbonylmethylphenyl))))adenosine (18.7 mg×μmol) was dissolved in 1 ml dimethylformamide and treated with 40 mg EDAC and 39 mg N-hydroxysuccinimide. After one hour, the reaction was complete as judged using thin layer chromatography (silica, chloroform:methanol:acetic acid, 85:10:5). The product (R$_f$ values for acid and ester, 0.32 and 0.40, respectively) precipitated slowly following cooling in an ice bath and addition of saturated sodium chloride. The product was isolated by centrifugation and washed with water, methanol, and ether. The product did not melt sharply, but decomposed at 175°. Yield 15 mg (68 %). The IR spectrum shows an intense ester carbonyl peak at 1740 cm$^{-1}$.

N$^6$-(4-(Bromomethylbenzoylglycylaminoethylaminocarbonylmethyl(phenyl(amino(4-carbonylmethylphenyl)))adenosine. N-Succinimidyl bromomethylbenzoyl-glycine (5 mg, 14 μmol) and ADAC upon addition of ether (3 ml). The product (8.6 mg, 74 % yield) melted at 211°–215°.

N$^6$-(4-(Fluoromethylbenzoylglycylaminoethylaminocarbonylmethyl(phenyl(amino(4-carbonylmethylphenyl)))adenosine, compound 24. N-Succinimidyl fluoromethylbenzoyl-glycine and ADAC reacted in DMF. A precipitate was isolated upon addition of The NMR spectrum was consistent with the assigned structure. FMB-purine derivatives 23 and 26 method of >300° and 275°, respectively.

Succinimidyl p-hydroxymethyl benzoate was prepared through a carbodiimide condensation. Mp. 151°–154°.

Ethyl p-hydroxymethylbenzoate. P-hydroxymethylbenzoic acid (1.66 g, 11 mmol, Chemical Dynamics Corp., South Plainfield, N.J.) was dissolved in absolute ethanol (30 ml) and treated with HCl gas. After 12 hours, the solvent was evaporated leaving the product (2.0 g, 100% yield) as an oil. CIMS peaks at 198, 181.

p-Hydroxymethylbenzoylaminoethylamine acetate. Ethyl p-hydroxymethylbenzoate (0.51 g, 2.8 mmol) was dissolved in ethylene diamine and heated on a steam bath overnight. The volume was reduced under a stream of nitrogen and the residue was chromatographed by preparative thin layer chromatography (silica, CHCl₃: MeOH:HOAc, 10:10:1) to yield the product as an oil (0.35 g, 49% yield).

N-t-Butyloxycarbonyl p-hydroxymethylbenzoylaminoethylamine. p-Hydroxymethylbenzoylaminoethylamine acetate (0.30 g, 1.2 mmol) in methanol was treated with di-t-butyloxycarbonyl dicarbonate (0.38 g, 1.8 mmol). The solvent was evaporated, and the residue was dissolved in ether. The ether solution containing the product was filtered and reduced in volume leaving a white solid, which was removed by filtration and washed with petroleum ether. Yield 0.34 g (99%). Mp 117°–119°.

N-t-Butyloxycarbonyl p-(methanesulfonyloxymethyl)benzoyl-aminoethylamine. N-t-Butyloxycarbonyl p-hydroxymethylbenzoylaminoethylamine was treated with mesyl chloride and one equivalent of diisopropylethylamine in dry pyridine to give the O-mesylate. The mesylated could be displaced by fluoride (tetrabutylammonium salt) in acetonitrile to give a product identical to compound 12 (n=2).

The process according to the present invention may be used with a great variety of compounds that bind to receptors in the body. Therefore, the compounds produced by the process of the present invention can be used to as probes in PETT scanning or like scanning techniques.

For the purposes of the present invention, a drug includes any compound that binds to a receptor. These drugs may be attached to carrier molecules and still retain their ability to bind to the receptor site to produce a biological effect. A particular strategy for the design of carrier-bound drugs is the functionalized congener approach, by which new analogs are synthesized with the regiospecific inclusion of a chain containing a chemical functional group in the terminal position attached at a nonsensitive position. The attached chain must not interfere sterically at the binding site for the pharmacophore. Simple derivatives of such a functionalized congener indicate how biological activity is affected using that site of attachment and what structural features may be desirable in a further elongated chain. The resulting chemically functionalyzed drug congener then may be attached through an amine or other reactive group on the chain to various organic moieties, such as amines and peptides. Surprisingly, the receptor binding affinity of these analogs is often greater than that of the parent drug and does not necessarily diminish as the molecular weight is increased. Moreover, an energetically favorable interaction, such as a hydrogen bond or a nonspecific interaction, between the attached group and the receptor molecule or a nearby membrane component may occur, thus increasing the strength of binding of the conjugate.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A process for making fluorinated compounds including ¹⁸F radiotracers from compounds containing an amino group comprising the steps of:
    coupling a compound containing a p-bromoethyl benzoyl group to a compound containing an amino group to form a first compound; and
    fluorinating said first compound so as to substitute the bromine atom in the p-bromomethyl benzoyl group with a fluorine atom to form said fluorinated compounds.

2. The process of claim 1, wherein the coupling is through an N-hydroxysuccinimide ester.

3. The process of claim 1 wherein the compound containing an amino group is an amino acid.

4. The process of claim 1 wherein the compound containing an amino group is a peptide.

5. The process of claim 1 wherein the fluorination reaction is conducted in a non-reactive polar aprotic solvent.

6. The process of claim 1 wherein the compound containing an amino group is a drug.

7. The process of claim 1 wherein the compound containing an amino group is insulin.

8. The process of claim 1 wherein the compound containing an amino group is a compound which can bind to a receptor in the human body.

9. A process for making fluorinated compounds including ¹⁸F radiotracers from compounds containing an amino group comprising the steps of:
    fluorinating a first compound containing a p-bromomethyl benzoyl group to form a first fluorinated product, wherein the bromine atom is substituted with a fluorine atom; and
    coupling said first fluorinated product to a compound containing an amino group to form the fluorinated compounds.

10. The process of claim 9 wherein the coupling is through an N-hydroxysuccinimide ester.

11. The process of claim 9 wherein the compound containing an amino group is an amino acid.

12. The process of claim 9 wherein the compound containing an amino group is a peptide.

13. The process of claim 9 wherein the fluorination reaction step is conducted in a non-reactive polar aprotic solvent.

14. The process of claim 9 wherein the compound containing an amino group is a drug.

15. The process of claim 9 wherein the compound containing an amino group is insulin.

16. The process of claim 9 wherein the compound containing an amino group is a compound which can bind to a receptor in the human body.

17. The process of claim 1 wherein the compound containing an amino group includes a spacer chain between the amino group to be attached to the bromomethyl benzoyl group and the amino group.

18. The process of claim 17 wherein the spacer chain is selected from the group consisting of alkyldiamines and diethylenetriamine.

19. The process of claim 1 wherein the amino group is blocked with a transient protecting group.

20. The process of claim 19 wherein the transient protecting group is t-butyloxycarbonyl.

21. The process of claim 9 wherein said coupling step includes esterifying said benzoyl group of said first compound with a succinimidyl group and then displacing the succinimidyl group with the compound containing an amino group.

22. The process of claim 9 wherein the first compound is fluorinated with $^{18}F$.

23. The process of claim 9 wherein the compound containing an amino group is an adenosine compound.

24. The process of claim 9 wherein the compound containing an amino group is a catecholamine compound.

25. The process of claim 9 wherein the compound containing an amino group is an indole compound.

26. The process of claim 9 wherein the compound containing an amino group is a purine compound.

* * * * *

UNITED STATES PATENT AND TRADEMARK OFFICE
CERTIFICATE OF CORRECTION

PATENT NO. : 5,098,996

DATED : March 24, 1992

INVENTOR(S) : Kenneth A. JACOBSON, Kenneth L. KIRK, David C. FURLAND and Yechiel SHAI It is certified that error appears in the above-indentified patent and that said Letters Patent is hereby corrected as shown below:

Column 2, line 68, after "acetonitrile at 23 C.", insert --The concentration of the fluoride is 0.5M and the initial concentration of the methylamide is 4.4mM.--

Signed and Sealed this

Twenty-sixth Day of July, 1994

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,098,996

DATED : March 24, 1992

INVENTOR(S) : Kenneth A. JACOBSON, Kenneth L. KIRK, David C. F FURLAND and Yechiel SHAI It is certified that error appears in the above-indentified patent and that said Letters Patent is hereby corrected as shown below:

Column 2, line 68, after "acetonitrile at 23 C.", insert --The concentration of the fluoride is 0.5M and the initial coneentration of the methylamide is 4.4mM.--

Signed and Sealed this

Eleventh Day of April, 1995

Attest:

BRUCE LEHMAN

*Attesting Officer*   *Commissioner of Patents and Trademarks*